Figure 1:
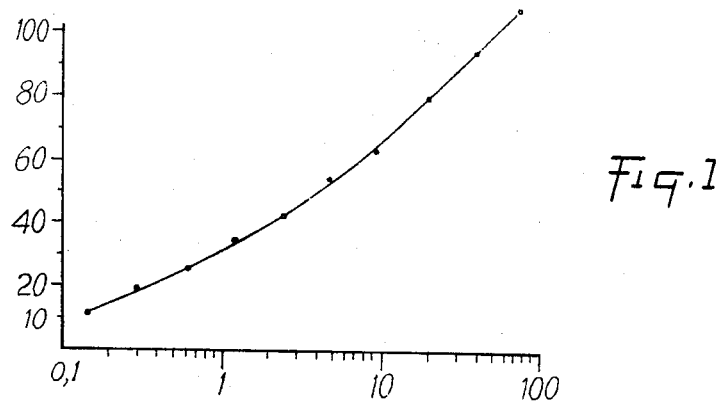

United States Patent [19]

Duheille et al.

[11] Patent Number: 4,690,906

[45] Date of Patent: Sep. 1, 1987

[54] NEPHELOMETRIC DETERMINATION OF $HB_s$ ANTIGEN WITH ANTIBODY-CONTAINING MICROPARTICLES

[75] Inventors: Jean Duheille, Saint-Max; Bernard Pau; Pierre Gros, both of Montpellier, all of France

[73] Assignee: Sanofi, Paris, France

[21] Appl. No.: 696,474

[22] Filed: Jan. 30, 1985

Related U.S. Application Data

[62] Division of Ser. No. 522,533, Aug. 12, 1983, abandoned.

[30] Foreign Application Priority Data

Aug. 16, 1982 [FR] France .................................. 82 14170

[51] Int. Cl.$^4$ ................. G01N 33/546; G01N 33/547; G01N 33/576
[52] U.S. Cl. ........................................ 436/512; 435/5; 435/7; 435/810; 436/517; 436/533; 436/534; 436/548; 436/805; 436/808; 436/820; 526/312; 526/315; 935/110
[58] Field of Search ............... 436/517, 533, 534, 805, 436/820, 512, 5, 548, 808; 435/5, 7; 935/110; 526/3, 5

[56] References Cited

U.S. PATENT DOCUMENTS

| | | |
|---|---|---|
| 3,553,310 | 1/1971 | Csizmas . |
| 3,957,741 | 5/1976 | Rembaum . |
| 3,985,632 | 10/1976 | Rembaum . |
| 3,992,517 | 11/1976 | Lowke ............................ 436/820 X |
| 4,046,720 | 9/1977 | Rembaum . |
| 4,093,602 | 6/1978 | Kalal . |
| 4,189,464 | 2/1980 | Blumberg ....................... 436/820 X |
| 4,305,925 | 12/1981 | Kapmeyer ...................... 436/805 X |
| 4,413,070 | 11/1983 | Rembaum . |
| 4,438,239 | 3/1984 | Rembaum . |

FOREIGN PATENT DOCUMENTS 2259847 8/1975 France .

*Primary Examiner*—Sidney Marantz
*Attorney, Agent, or Firm*—Bacon & Thomas

[57] ABSTRACT

The present invention relates to polyfunctional hydrophilic spherical microparticles of uniform size which contain from 5 to 95% of units originating from the copolymerization of an aldehyde of the formula

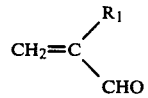

$R_1$ being an alkyl radical, from 5 to 90% of units originating from the copolymerization of an acrylic acid ester of the formula

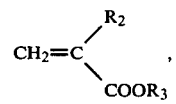

in which $R_2$ is H or alkyl and $R_3$ is a hydroxyalkyl group, less than 15% of units originating from an acrylic acid derivative chosen from amongst

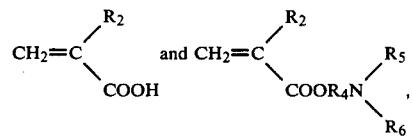

$R_4$, $R_5$ and $R_6$ being alkyl radicals, and from 0.1 to 10% of units originating from a crosslinking product.

The invention also relates to a process for the preparation of the said microparticles and to the use of these microparticles for the nephelometric determination of $HB_s$ antigen.

13 Claims, 3 Drawing Figures

NEPHELOMETRIC DETERMINATION OF HB$_s$ ANTIGEN WITH ANTIBODY-CONTAINING MICROPARTICLES

This application is a division of application Ser. No. 522,533 filed Aug. 12, 1983, now abandoned.

The present invention relates to reagents which can be used for the diagnosis of type B viral hepatitis, to a process for the preparation of these reagents and to a process for using these reagents for carrying out the quantitative determination, with very high sensitivity, of the antigen characteristic of hepatitis B virus in human serum.

Viral hepatitis is a very common, transmissible infectious disease which is caused by a virus and which is usually characterized by necrosis and inflammation of the liver, frequently accompanied by jaundice. Although this disease is generally benign, almost 1% of cases are fatal and about 5% of cases lead to prolonged or chronic forms. A distinction is drawn between type A hepatitis, whose virus is mainly transmitted orally (food, drink), type B hepatitis, whose virus is most frequently transmitted parenterally, and, finally, other forms of hepatitis (neither A nor B). As regards type B hepatitis, the subjects most likely to contract the disease are those undergoing blood transfusions or hemodialysis, medical and paramedical personnel and personnel at blood transfusion centers. All blood donors are therefore systematically screened for hepatitis B virus because it is known that the virus can persist for a long time in the blood of apparently healthy subjects.

The observed correlation between the increase in sensitivity of the screen techniques and the reduction in the frequency of post-transfusional hepatitis argues very strongly in favor of making available reagents and determination techniques of high sensitivity which are easy to carry out, have a rapid response time and are inexpensive.

Attention should also be drawn to the correlation which exists, in particular in certain African populations, between the presence of hepatitis B virus in the blood and the appearance of primitive liver cancers. This observation also argues in favor of creating the possibility of mass diagnosis in these populations.

The surface antigen of hepatitis B virus, which is called HB$_s$ antigen or Australia antigen, is generally recognized as the most important marker of the virus, and it is this antigen which it is sought to determine in the blood. The currently available methods for achieving the required sensitivity - the detection threshold must be below 1 nanogram per milliliter of serum - are all of the radioimmunological type and, in particular, have the following disadvantages associated with the handling of radioactive substances: specialized and expensive equipment, possible contamination problems (detrimental to the quality of the result and the safety of the personnel), the obligation to have personnel who are highly qualified and monitored from the medical and radiotoxicological points of view, legally imposed constraints regarding the fitting out of the premises and safety, the limited shelf life of the reagents, and so on.

The reagents and processes to which the present invention relates are radically different in nature since they do not involve any handling of radioactive substances by the user and therefore avoid all the above-mentioned disadvantages. The principle chosen for these determinations is that of very high sensitivity nephelometry on a microparticulate support.

Nephelometry is a physical method very widely known in analytical chemistry. When the same principle is applied to the quantification of antigen/antibody reactions, it is then called immunonephelometry. It has been employed mainly for the specific determination of proteins in serum by measuring the intensity of the light scattered by the insoluble immune complexes formed between each of these proteins and a corresponding immunoserum. The improvements in equipment, in particular by the use of laser light sources, has made it possible to achieve sensitivities of the order of a microgram of protein to be determined per ml of biological liquid.

Instruments of this type are now widespread in laboratories, but the sensitivity thereby achieved is still very inadequate for the determination of HB$_s$ antigen.

As early as 1976, BONNEFOY and GRANGE (C.R. Acad. Sc. Paris D 283, 1976, 115-118) proposed improving the performance characteristics of immunonephelometry by the use of polystyrene microspheres carrying one of the components of the antigen/antibody reaction to be studied. This modification introduces the principle of using microparticulate supports in immunonephelometry.

Similar studies have formed the subject of publications (see, in particular, J. Immunol. Methods 18, 1977, 214-224; ibid 33, 1980, 159-173; Immunochemistry 13, 1976, 955-962 and 963-966; Molec. Immunol. 17, 1980, 81-92) and of patents (in particular the patent filed in France in the name of INSERM (inventor G. A. QUASH) of 06/03/79). These techniques preferably employ polystyrene microspheres to which the component appropriate to the antigen/antibody reaction to be studied is fixed (by adsorption or by covalent bonding).

The performance characteristics have been further improved by the use of microparticulate supports of hydrophilic character, in contrast to the previous supports which were hydrophobic and exhibited instability through self-agglutination and slow sedimentation and risks associated especially with non-specific adsorptions. These new hydrophilic microparticulate supports have been described and patented, in particular, by REMBAUM and coworkers (REMBAUM et al. Macromolecules 9 (2), 1976, 328-336; REMBAUM et al. J. Macromol. Sci. Chem. A 13 (5), 1979, 603-632; French Patent No. 2,258,406 of Jan. 17th 1975; U.S. Pat. No. 4,138,383 of Feb. 6th 1979 and U.S. Pat. No. 4,206,094 of Jan. 3rd 1980), but these were for biomedical purposes not related to immunonephelometry or to the determination of HB$_s$ antigen. Supports of the same type have also been used by DUHEILLE and coworkers (MONTAGNE et al. Laser Behring Study Group, September 1979; MONTAGNE et al. 4th International Immunology Congress—Paris July 21st–26th 1980) for the immunonephelometric determination of circulating immune complexes. However, no technique of this type has ever been applied to the determination of HB$_s$ antigen.

Pursuing its studies on the formation of the nephelometric signal as a function of the size, number and characteristics of the dispersing particles, the Applicant Company has discovered the great advantage of new microparticulate supports which behave as noteworthy indicators and amplifiers of the nephelometric signal. It is these supports and their application to the determination of HB$_s$ antigens which form the subject of the present invention. These new supports have the following characteristics and advantages:

1. They are polyfunctional hydrophilic spherical microparticles with an electric charge which can be varied in a controlled manner, and with a size which is very uniform and can be perfectly controlled within the average diameter range from about 10 nanometers to about 10 micrometers.

2. Such characteristics, which are outstandingly favorable for the desired purpose and which, as a whole are not possessed by any of the supports described previously, are a consequence of the chemical nature of these particles, which result from the copolymerization, carried out in a strictly aqueous medium, of at least three watersoluble acrylic monomers in the presence of a crosslinking agent and a surface-active agent, which are themselves also water-soluble.

All the characteristics of these particles, namely geometric characteristics (average size and size distribution around the average), physical characteristics (hydrophilicity and density of surface electrical charges) and chemical characteristics (chemical functional groups present on the surface), are entirely governed by the choice of the nature of the constituents of the reaction medium, their relative proportions and the conditions under which the copolymerization takes place.

3. The acrylic monomers used are chosen from amongst the substances defined below:

(a) An acrylic aldehyde of the general formula:

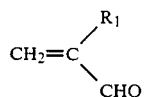

in which $R_1$ is hydrogen or a lower alkyl group. This monomer can represent from 5 to 95% by weight of all the monomers, but most frequently between 40 and 60%.

It provides aldehyde groups which will be preserved during the polymerization and will be present and accessible on the surface of the microspheres obtained, thus making it possible to simplify and diversify the procedures for the coupling, by covalent bonding, of proteins or glycoproteins, or of other appropriate natural or semi-synthetic macromolecules or molecules on the surface of the microspheres.

(b) A carboxylic acrylic acid derivative of the general formula:

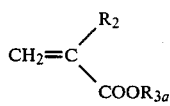

in which $R_2$ is hydrogen or a lower alkyl group and $R_{3a}$ is hydrogen.

This monomer can represent from 0 to 15% by weight of all the monomers and provides the microspheres with carboxyl groups whose anionic character, at physiological pH, is essential to the regulation of the surface electrical charge of the microspheres and hence to the stability of the reagent in suspension. All or some of these carboxyl groups can also be used as chemical functional groups available for effecting the covalent coupling of the molecules to be fixed to the microspheres, in accordance with the conventional chemical techniques.

(c) Another acrylic acid derivative of the general formula:

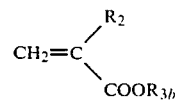

in which $R_2$ has the same meaning as above and $COOR_{3b}$ represents a group of the structure:

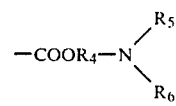

in which $R_4$, $R_5$ and $R_6$ are identical or different lower alkyl groups.

This monomer can represent from 0 to 15% by weight of all the monomers and provides the microspheres with tertiary amine groups whose cationic character, at physiological pH, contributes to the regulation of the surface electrical charge of the microspheres and hence to the stability of the reagent in suspension.

(d) Another acrylic acid derivative of the general formula:

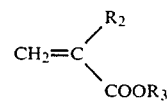

in which $R_2$ has the same meaning as above and $R_3$ is a lower hydroxyalkyl group.

This monomer can represent from 5 to 90% by weight of all the monomers and most frequently between 40 and 70%. It provides a large number of hydroxyl groups which give the microspheres their hydrophilicity and makes them perfectly wettable by aqueous solvents, this also contributing to the stability of the reagent.

The products according to the invention will therefore be obtained from at least three monomers, namely the monomers (a) and (d) and at least one of the monomers (b) and (c); in other words, the amounts of (b) and (c) used cannot simultaneously be zero.

It is thus obvious that, by carefully choosing the proportion of the monomers belonging to the classes (b), (c) and (d) defined above, both the hydrophilicity and the net The products include polyfunctional hydrophilic spherical microparticles of uniform size and with average diameters of between about 10 nanometers and about 10 micrometers, which contain:

1. from 5 to 95% and preferably from 40 to 60% by weight of units originating from the copolymerization of an acrylic aldehyde of the formula

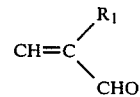

in which $R_1$ is an alkyl radical having from 1 to 4 carbon atoms, 2. from 5 to 90% and preferably from 40 to 70% by weight of units originating from the copolymerization of an acrylic acid derivative of the formula

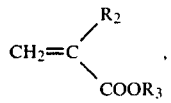

in which $R_2$ is chosen from amongst hydrogen and alkyl groups having from 1 to 4 carbon atoms and $R_3$ is a lower hydroxyalkyl radical, 3. less than 15% by weight of at least one acrylic acid derivative chosen from amongst the derivatives of the formulae

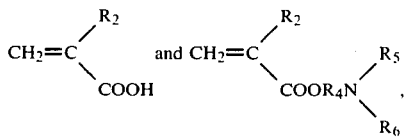

in which $R_4$, $R_5$ and $R_6$ are identical or different lower alkyl groups (1 to 4 carbon atoms), and from 0.1 to 10% and preferably from 0.5 to 5% by weight of units originating from a crosslinking agent which is an unconjugated diene, in particular N,N'-methyl-ene-bis-acrylamide.

A process for the preparation of the above microparticles comprises carrying out the copolymerization, in an aqueous medium, of monomers in the following relative proportions:

1. from 5 to 95% and preferably from 40 to 60% by weight of units originating from the copolymerization of an acrylic aldehyde of the formula

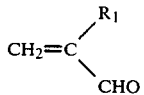

in which $R_1$ is an alkyl radical having from 1 to 4 carbon atoms, 2. from 5 to 90% and preferably from 40 to 70% by weight of units originating from the copolymerization of an acrylic acid derivative of the formula

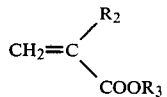

in which $R_2$ is chosen from amongst hydrogen and alkyl groups having from 1 to 4 carbon atoms and $R_3$ is a lower hydroxyalkyl radical, 3. less than 15% by weight of at least one acrylic acid derivative chosen from amongst the derivatives of the formulae

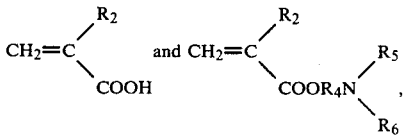

in which $R_4$, $R_5$ and $R_6$ are identical or different lower alkyl groups (1 to 4 carbon atoms), and from 0.1 to 10% and preferably from 0.5 to 5% by weight of units originating from a crosslinking agent which is an unconjugated diene, in particular N,N'-methyl-ene-bis-acrylamide, the said copolymerization being carried out in the presence of a water-soluble surface-active agent.

It is thus obvious that, by carefully choosing the proportion of the monomers belonging to the classes (b), (c) and (d) defined above, both the hydrophilicity and the net electrical charge of the microspheres can be regulated exactly as desired. This regulation is essential to enable the reagent to achieve the maximum sensitivity of the determination. In fact, the sensitivity of the determination will be a maximum if the electrical charge of the microspheres is regulated in such a way that the electrostatic repulsions between spheres are just strong enough to prevent self-aggregation, but weak enough to allow the specific agglutination of two spheres by the minimum antigen/antibody reaction. The same conditions also favor acceleration of the specific agglutination reactions, and this represents a very favorable factor when carrying out the determination in practice.

Finally, it must be noted that the absence of any hydrophobic monomer makes it possible to obtain a homogeneous aqueous reaction medium which favors the greatest uniformity in the initiation and subsequent course of the polymerization, resulting in an excellent homogeneity in the size of the spheres formed, irrespective of the average size which it is desired to obtain.

4. In addition to the acrylic monomers described above, the polymerization medium contains a crosslinking agent for forming the bridges between linear chains of acrylic polymers and thus providing the cohesion of the three-dimensional copolymer network. This crosslinking agent is a water-soluble unconjugated diene, in particular N,N'-methylene-bis-acrylamide, and represents from 0.1 to 10% by weight of all the monomers and most frequently between 0.5 and 5%. The chosen proportion of crosslinking agent also serves to control the porosity of the microspheres obtained.

5. Finally, the polymerization medium contains a surface-active agent which can be of ionic type - in particular sodium dodecyl-sulfate - or of non-ionic type. It is used at a concentration of between 0.01% and 5% by weight of the total reaction medium and its main function is to regulate the modes of growth of the spheres during the polymerization, and hence the final size of the microspheres obtained.

6. In the course of our surveys, it was recognized that the final size of the microspheres obtained could be most favorably regulated by varying on the one hand the surface-active agent concentration and on the other hand the final concentration of total monomer mixture in the polymerization reaction medium. All other things being equal, the diameter of the microspheres obtained is the greater the lower the surface-active agent concentration and the higher the total monomer concentration. The total monomer concentration in the reaction medium can be chosen between 4 and 16% by weight.

7. When the chosen monomers, the crosslinking agent and the surface-active agent have been mixed under conditions making it possible to obtain microspheres having the desired characteristics, this reaction medium is divided up into borosilicate glass ampoules of appropriate size, which are then sealed in vacuo. These ampoules are fixed to a shaker of the reciprocating or rotary type and the whole is placed in the irradiation chamber of a cobalt 60 bomb. The irradiation which causes the polymerization reaction is carried out at a rate of 0.01 to 0.5 megarad per hour and per cm$^3$ of reaction medium for a period which is never less than 15 minutes and can be as much as 10 hours.

Our studies have also shown that, at a constant radiation dose, the size of the beads is greater if the flux is lower and the irradiation period correspondingly longer.

After irradiation, the ampoules are opened and the reaction medium is diluted in an equal volume of a reducing aqueous solution (in particular a solution containing 1 g/liter of hydroquinone) in order on the one hand to stop the polymerization reactions and on the other hand to prevent oxidation of the aldehyde groups present on the microspheres. The preparations obtained are then perfectly stable and are kept at 4° C. under these conditions for subsequent use. The microspheres obtained can be examined and checked by electron microscopy, which makes it possible to determine both the average size and the size distribution around this average. Under the conditions employed, the standard deviation of the sizes for a given preparation is always less than a tenth of the average.

In order to be used for the determination of $HB_s$ antigen, the microspheres obtained must also have been chemically coupled beforehand with the antibodies which are directed against the $HN_s$ antigen and which will cause the specific agglutination reaction on which the formation of the nephelometric signal is based. The antibodies which can be used according to the invention are:

either polyclonal and isolated by the known techniques from specific immune sera obtained from animals after immunization with purified $HN_s$ antigen, or monoclonal and purified by the known methods after production from hybrid cells (hybridomas) resulting from the fusion of plasmocytes of animals immunized against $HB_s$ antigens, and from myeloma cells possessing the appropriate characteristics.

The antibodies which can be used can also result from mixtures of several immunoglobulins specific to $HB_s$ antigen, so as not to allow any rare variant of the antigen to escape the determination.

In order to couple the anti-$HB_s$ antibodies with the chosen microspheres, the suspension of microspheres is dialyzed beforehand to remove the excess reagents and is then adjusted to a known concentration of between 1 and 50 mg of particles per ml (concentration determined by dry weight) in an isotonic buffered medium and treated with a solution of the antibody in the same solvent. The coupling takes place spontaneously in a few hours at ambient temperature by reaction of the amino groups of the protein with the aldehyde groups carried by the microspheres, to form imine linkages.

After the reaction has reached the required degree of completion (between 1 and 30 hours), the excess aldehyde groups are blocked by reaction with an excess of a primary amine, preferably a primary hydroxyamine, such as ethanolamine, in which the hydroxyl groups also contribute to the hydrophilicity of the particles coated in this way. This step is carried out by incubation at ambient temperature for a further 1 to 10 hours.

Alternatively, the step for blocking the excess aldehyde groups can be replaced by a reduction step using a metal hydride, in particular sodium borohydride. This treatment causes the reduction of the imine groups to secondary amine groups, which stabilizes the fixing of the antibody to the microspheres, and at the same time reduces the aldehyde groups to alcohol groups, which, as above, favors the hydrophilicity of the particles.

The suspension of the microspheres thus obtained is then purified by centrifugation in the presence of an appropriate density gradient (for example a sucrose gradient of 10 to 60%). The layer containing the particles is recovered and finally dialyzed against an isotonic buffer.

This type of preparation of immunospheres (microspheres carrying a specific antibody) can be used directly for the nephelometric determination of $HB_s$ antigen in any human biological liquid, in particular serum or plasma, which may have been suitably diluted. The procedure is that which is conventionally employed, where, after the antigen/antibody reaction has taken place, the nephelometric signal given by the dish containing the unknown sample is compared with a standardization curve produced by measuring the signals obtained in the presence of known amounts of the standard antigen.

All the technical facilities offered by modern laser nephelometers, such as the automatic subtraction of a blank, the possibilities of carrying out kinetic measurements or end point measurements, automation, miniaturization, incorporated computers, electronic signal processing, and the like, can of course be utilized in order to obtain results of the best possible quality in the particular application forming the subject of this invention. Moreover, and taking account of the fact that instruments of different makes do not have identical characteristics and facilities, it is possible to take advantage of the very great flexibility offered by the process forming the subject of the present invention, in order to optimize the preparation of the reagents and adapt them to each type of equipment so as to ensure the maximum performance characteristics.

The examples which follow provide a clearer understanding of the invention without limiting its scope.

EXAMPLE 1

Preparation of microspheres with average diameters of 50, 110 or 190 nanometers:

All the reagents used are obtained commercially and are carefully redistilled just before use. The general procedure employed is as follows: borosilicate glass sealing ampoules with a diameter of 35 mm and a total capacity of 150 ml are prepared and the desired amounts of each of the monomers, the crosslinking agent, the surfaceactive agent and water, degassed in vacuo beforehand, are introduced into each ampoule so as to give, in every case, 100 ml of media having the respective compositions given in Table 1. After a stream of nitrogen has been bubbled through, the reaction media are frozen by immersion in liquid nitrogen and the ampoules are immediately sealed in vacuo. The polymerization is caused by irradiation with γ rays in a $^{60}CO$ bomb. The radiation fluxes and the irradiation times are also given in Table 1. Throughout the irradiation, the ampoules are fixed to a shaker with a plate rotating at 20 rpm and are arranged so as to ensure the greatest homogeneity of irradiation. Dosimeters arranged in the irradiation chamber make it possible to check the radiation doses. After polymerization, the ampoules are opened and their contents poured into an equal volume of an aqueous solution containing 1 g/liter of hydroquinone. The preparations are simply kept under these conditions in a well-stoppered vessel and at 4° C. until they are used. The diameter of the microspheres is determined on preparations examined by electron microscopy.

TABLE I

| | Size of the microspheres (nm) | | |
|---|---|---|---|
| | 50 | 110 | 190 |
| | Composition of the reaction media (% by weight of the total monomers) | | |
| Acrolein | 45.1 | 47.0 | 47.0 |
| Hydroxyethyl methacrylate | 51.3 | 49.7 | 50.7 |
| Methacrylic acid | 2.3 | 2.0 | 1.0 |
| N,N'—Methylene-bis-acrylamide | 1.3 | 1.3 | 1.3 |
| Total monomers (% of the total volume of the medium) | 7.4 | 8.0 | 12.0 |
| Sodium dodecyl-sulfate (g/liter of final medium) | 0.60 | 0.60 | 0.90 |
| Radiation flux ($krad.ml^{-1}.min^{-1}$) | 0.9 | 0.3 | 1.1 |
| Irradiation time (hours) | 1.5 | 1.5 | 1.5 |

EXAMPLE 2

Coupling of the anti-$HB_s$ monoclonal antibodies with the microspheres of diameter 50 nm:

(a) Monoclonal antibodies:

The preparation of monoclonal antibodies used in this experiment consists of a mixture of anti-$HB_s$ monoclonal mouse immunoglobulins (of class G and sub-classes 1, 2a and 2b), purified on a column of Staphylococcus protein A immobilized on Sepharose, from the ascitic fluids of mice in which five different hybridomas producing monoclonal antibodies specific to $HB_s$a antigen had been respectively implanted (in the peritoneum).

(b) Coupling:

The suspension of microspheres of diameter 50 nm prepared as indicated in Example 1 is first rendered isotonic by the addition of sodium chloride to a final concentration of 140 mM and is then exhaustively dialyzed against an isotonic buffer (PBS) consisting of 10 mM phosphate buffer containing sodium chloride at a concentration of 140 mM and adjusted to pH 7.2. This buffer is carefully degassed before use. An aliquot of the suspension obtained is also dialyzed against pure water in order to determine the concentration, by dry weight, of microspheres in the suspension.

For the coupling, an aliquot of suspension of microspheres in the PBS buffer, containing 11 mg of particles, is added to an aliquot of anti-$HB_s$ antibody solution containing $10^{-8}$ mole of immunoglobulins in the same buffer, and the total volume is made up to 1 ml with PBS buffer. After 18 hours at ambient temperature, with very gentle shaking, 200 microliters of a 0.2 M ethanolamine solution adjusted to pH 7.2 with hydrochloric acid are added and the medium is kept under the same conditions for a further 2 hours.

The reaction medium is placed in a centrifuge tube containing a preformed sucrose gradient of 10 to 60% (weight per volume) and the tube is centrifuged for 2 hours at 4° C. and at 20,000 rpm. The layer containing the microspheres is removed and the microspheres are dialyzed against 3 times 1 liter of PBS buffer.

EXAMPLE 3

Use of the anti-$HB_s$ immunospheres for the nephelometric determination of $HB_s$ antigen.

(a) Equipment used:

For the experiments described, the equipment used is the PDQ HYLAND laser nephelometer equipped with an He/Ne laser having a power of 0.5 mW at 632.8 nm and measuring the light intensity at an angle of observation of 31.8° relative to the axis of the incident beam. The dishes make it possible to work with a total volume of 1 ml.

(b) General conditions of the tests

In all cases, the total volume of medium in the dish is 1 ml. The immunospheres obtained as indicated in Example 2 are introduced in the form of 100 microliters of an appropriate dilution of the mother suspension, which are finally added to the mixture prepared in the dish and containing the sample to be examined, suitably diluted in PBS buffer containing 1 g/liter of bovine serum albumin and 1 g/liter of Tween 80 and made up to a total volume of 900 microliters with the same diluent. The specific agglutination reaction generating the nephelometric signal starts when the immunospheres are added and can be followed with time (kinetic observation) or measured at a set time. Unless indicated otherwise, the measurement is made 1 hour after the specific immunospheres have been brought into contact with the antigen in the dish. The experiment showed that the essential part of the specific nephelometric signal has been obtained after this time and that extension of the time to 8 or 16 hours does not bring any substantial practical advantage. All the results presented below are given after subtraction of the blanks corresponding to each test, and therefore represent the specific signal of the reaction evaluated.

(c) Samples used a reference human serum containing 31 micrograms of $HB_s$ antigen per milliliter, and a positive human serum originating from a hospital, containing about 5 micrograms per ml.

(d) Studies carried out

1° Stability of the suspensions of immunospheres:

The signals corresponding to four different suspensions of anti-$HB_s$ immunospheres by themselves (without antigen), having concentrations of between 3.5 and 28 μg/ml, were measured repeatedly over a period of 96 hours, without shaking the contents of the dishes. These signals proved to be of excellent stability since the extreme values observed never deviate by more than 2% from the average value for the most concentrated suspension and by more than 7% for the most dilute suspension. This result shows the extreme stability of the suspensions of immunospheres under the practical conditions of their use and for periods incomparably longer than those which are necessary for the analytical applications. 2° Standardization of the determination:

2-1. If the concentration of the immunospheres is fixed at 7 micrograms per milliliter, a standardization range drawn up using dilutions of the standard serum shows that the specific nephelometric signal makes it reasonable to explore an extremely vast range of antigen $HB_s$ concentrations since this range extends from about 0.15 ng/ml up to almost 80 ng/ml. This standardization curve is shown in FIG. 1, in which the scattered light intensity has been plotted on the ordinate (in arbitrary units) and the antigen $HB_s$ concentration has been plotted on the abscissa in nanograms per milliliter.

This characteristic is of great practical value inasmuch as it prevents the user from having to prepare a large number of dilutions of an unknown sample in order to obtain a measurement within the usable part of the standardization range.

Figure 2:
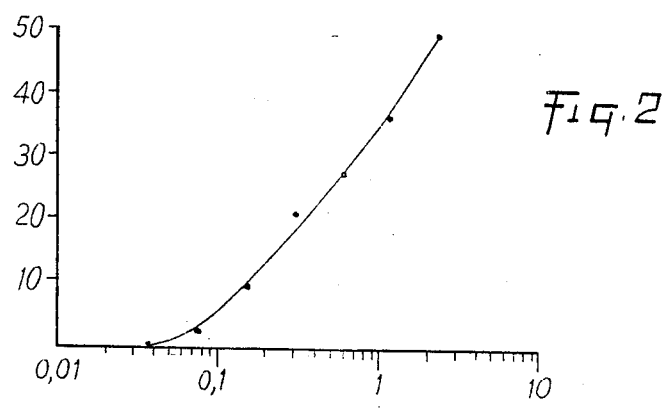

2-2. If the concentration of the immunospheres is lowered to 1.4 micrograms per milliliter, a similar standardization curve shows that the limiting sensitivity can easily be lowered to an antigen concentration of the order of 0.1 ng/ml or even less. This standardization curve is shown in FIG. 2, in which the scattered light intensity has been plotted on the ordinate (in arbitrary units) and the $HB_s$ antigen concentration has been plotted on the abscissa in nanograms per milliliter. This result is extremely important since it shows that the perfected method makes it possible to achieve limiting sensitivities at least as high as those of the best radioimmunological determinations currently available, without having any of the disadvantages associated with the handling of radioactive substances.

3° Specificity checks

If, under conditions identical to those in paragraph 2-1, the antigen solutions are incubated for 24 hours with free antibody (not coupled with the immunospheres) at a final concentration of 70 micrograms/milliliter, no signal distinguishable from the reagent blank appears. This shows that, when it is not coupled with the immunospheres, the specific antibody is incapable of causing the appearance of a specific nephelometric signal, even at high concentration.

If the specific immunospheres are then introduced into the same dishes, again no specific signal is seen to appear. This shows that the antigen present has indeed been neutralized by the excess free antibody in the first step and is therefore no longer available to cause the specific agglutination of the immunospheres in the second step. This result demonstrates the specificity of the immunospheres used in relation to recognition of the $HB_s$ antigen.

Figure 3:
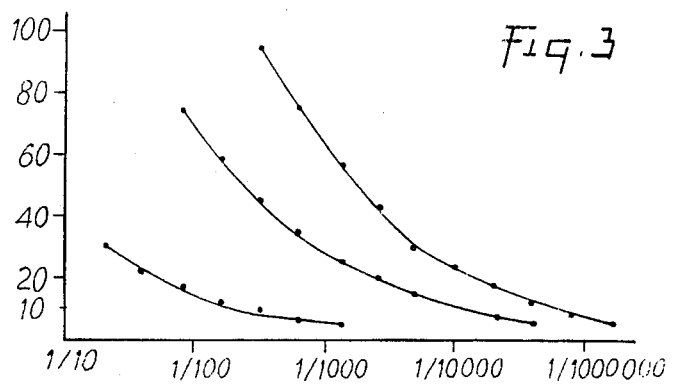

4° Determination of an unknown serum:

4-1. To permit a realistic evaluation of the ability of the reagents forming the subject of the present invention to provide a high degree of flexibility when used in the determination of $HB_s$ antigen in sera of unknown strength, a human serum originating from a hospital was employed. A series of 14 dilutions of this serum were prepared, in a geometric progression with a factor 2, and aliquots of all these dilutions were reacted with the immunospheres under the conditions described in paragraph 2-1. The curves in FIG. 3 show that the specific nephelometric signal of all these dilutions is easily measurable, provided that the appropriate sensitivity range of the instrument is selected, up to extremely high dilutions of starting serum, since the signal is still significant for a dilution of 1/100,000. This observation shows that, in practice, with a maximum of 5 dilutions, an unknown serum can be determined in a single step, the duration of which is not more than one hour, whatever its concentration within the range between 1 $\mu$g/ml and 10 $\mu$g/ml.

In this FIG. 3, the light intensity has been plotted on the ordinate in arbitrary units and the dilution of the serum has been plotted on the abscissa. The measurements were made with immunospheres at a concentration of 7 mg/ml and with three different sensitivities of the instrument.

4-2. In the actual case of the serum used, comparison of the signals obtained for the dilutions best located within the measuring range, with the standardization curve of FIG. 1, leads to an average value of the strength of the serum of 5.9 mg of $HB_s$ antigen per ml, the extreme values observed over 6 measurements, simply by way of example, at different dilutions, being 5.3 and 6.4. This precision is excellent for determinations of this type.

5° Repeatability of the results

Under conditions analogous to those indicated above, if the signals given 10 by dishes which are independent but of identical composition are measured for two different dilutions of serum and over the corresponding sensitivity ranges, statistical analysis of the values obtained leads to the following results:

|  | 1st dilution (1/40) | 2nd dilution (1/5120) |
|---|---|---|
| Number of measurements | 10 | 10 |
| Average signal (arbitrary units) | 52.2 | 69.5 |
| Standard deviation | 2.72 | 4.36 |
| Coefficient of variation (%) | 5.2 | 6.3 |

These results confirm the excellent repeatability of the determination as a whole, including, in particular, the agglutination reaction of the specific immunospheres by the antigen to be determined.

These various tests demonstrate the characteristics and advantages of the method for the determination of $HB_s$ antigen using the reagents and processes forming the subject of the present invention. In particular, they demonstrate:

the very great sensitivity of the determination, which reaches detection thresholds at least as low as those of the best methods currently available for this determination (of the order of 0.1 ng of antigen per ml);

the high specificity provided by choosing monoclonal antibodies which are strictly specific for the antigen to be determined;

the ease of carrying out the determination as a whole, whose operations are limited to a few micropipetting operations which can be carried out either by hand or in an entirely automated manner, as desired;

the very good keeping properties of the reagents, which have a shelf life of months (and probably years) at 4° C.;

the low cost price of each determination, which does not require highly qualified personnel and which only consumes extremely small amounts of reagents (from a few micrograms to a few tens of micrograms of immunospheres per test, depending on the instruments used);

the possibility of adapting the technique to all commercial laser nephelometers which are commonplace in laboratories, without significant loss of overall performance characteristics;

the short response time of the analytical manipulation as a whole, since the longest step is that required by the reaction of the antigen with the antibody, which cannot exceed one hour; and the versatility of the method: in fact, the examples described relate only to the direct determination of the antigen by agglutination of the immunospheres carrying the specific antibody. In accordance with a completely analogous principle, it is equally possible to couple the purified antigen with the microspheres. In that case, if microspheres carrying the antigen are introduced into the measuring dishes in a constant amount, and specific antibody is introduced, also in a constant amount, in order to ensure the specific agglutination generating the nephelometric signal, the resulting system is one in which any introduction of free antigen in the form of an appropriately diluted aliquot of a serum to be determined (or of a standard serum) will cause a measurable inhibition of the base signal, which makes it possible to carry out a quantitative determination by inhibition.

The reagent kits which will be marketed for application of the present invention will comprise the following in particular:

(a) for the direct measurement of the antigen:

The specific reagent in the form of immunospheres carrying the specific anti-$HB_s$ antibody, which may be polyclonal or may consist of one or more monoclonal immunoglobulins, either whole or in the form of fragments which have retained the ability to recognize the antigen. This reagent will be presented either in solution to be diluted, if appropriate, before use, or as a lyophilizate to be reconstituted before use in a solvent indicated to the user or delivered in the kit, it also being possible for all these preparations to contain additives such as preservatives and stabilizers.

(b) for the measurement of the antigen by inhibition:

Two specific reagents which are:

microspheres carrying the specific antigen and presented under conditions similar to those described for the specific immunospheres in case (a) above, and an agent capable of causing the agglutination, such as any suitable preparation containing a total anti-$HB_s$ antiserum or specific polyclonal or monoclonal anti-$HB_s$ immunoglobulins, purified or not purified and whole or in the form of fragments having the ability to recognize the specific antigen and to agglutinate the microspheres carrying the specific antigen. This agent will be presented either in buffered or non-buffered solution to be diluted, if appropriate, before use, or in the form of a lyophilizate to be reconstituted in a solvent indicated to the user or delivered in the kit, it also being possible for this preparation to contain additives such as preservatives and stabilizers.

In addition, whatever the method of determination adopted, the kit may comprise common reagents, which will be the following in particular:

a diluent, a standard preparation of $HB_s$ antigen, control preparations, such as, for example, control sera of low, medium and high concentration relative to the size of the normal determination range, and a negative control serum guaranteed free of $HB_s$ antigen.

These common reagents will be presented either in buffered or non-buffered solution to be diluted, if appropriate, before use, or in the form of lyophilizates to be reconstituted in a solvent indicated to the user or delivered in the kit. These preparations may also contain additives such as preservatives, stabilizers, surfaceactive agents and dispersing agents, it being possible, if appropriate, for all these additives to be macromolecular (and in particular of the protein type).

We claim:

1. A method for nephelometrically determining $HB_s$ antigen by contacting $HB_s$ antigen with antibody containing polyfunctional hydrophilic spherical microparticles of uniform size having an average diameter of between about 10 nanometers and about 10 micrometers, said microparticles comprise copolymers obtained by copolymerizing:

(a) from 5 to 95% by weight of the total monomers of an acrylic aldehyde having a formula

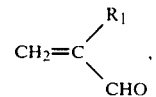

in which $R_1$ ia an alkyl radical having from 1 to 4 carbon atoms, (b) from 5 to 90% by weight of total monomers of an acrylic acid derivative having a formula

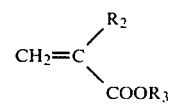

in which $R_2$ is hydrogen or an alkyl group having from 1 to 4 carbon atoms and $R_3$ is a lower hydroxyalkyl radical, (c) and less than 15% by weight of total monomers of at least one acrylic acid derivative having a formula:

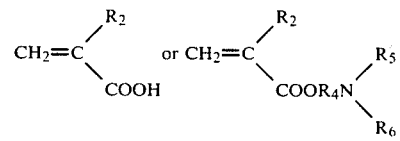

wherein $R_2$ is hydrogen or lower alkyl and $R_4$, $R_5$ and $R_6$, which may be the same or different, represent a $C_{1-4}$ alkyl group; and from 0.1 to 10% by weight of total monomers of an unconjugated diene crosslinking agent; said microparticles having coupled thereto an antibody selected from the group consisting of polyclonal antibodies isolated from specific immune sera obtained from animals after immunization with purified $HB_s$ antigen and monoclonal antibodies produced from hybrid cells resulting from the fusion of plasmocytes of animals immunized against $HB_s$ antigen, and from myeloma cells to obtain an antigen-antibody reaction which is nephelometrically measured.

2. A method as claimed in claim 1, for the nephelometric determination of $HB_s$ antigen in biological liquid.

3. A method as claimed in claim 1, wherein, after the microparticles have been coupled with the antibody, the product obtained is treated with an excess of a primary amine so as to block the free aldehyde groups.

4. A method as claimed in claim 3, for the nephelometric determination of $HB_s$ antigen in biological liquid.

5. A method as claimed in claim 1, wherein, after the microparticles have been coupled with the antibody, the product obtained is reduced by treatment with a metal hydride.

6. A method as claimed in claim 5, for the nephelometric determination of $HB_s$ antigen in biological liquid.

7. A method as claimed in claim 1, wherein the monomers of (a) and (b) are present in amounts of from 40–60%, and 40–70%, respectively, and from 0.5 to 5% of crosslinking agent is present.

8. A method as claimed in claim 7, wherein the crosslinking agent is N,N'methylene-bis-acrylamide.

9. A reagent kit for nephelometrically determining antigen by contacting antigen with antibody or antibody fragments, which comprises antibody or antibody fragment containing polyfunctional hydrophilic spherical microparticles of uniform size having an average diameter of between about 10 nanometers and about 10 micrometers, said microparticles comprise copolymers obtained by copolymerizing:

(a) from 40 to 60% by weight of the total monomers of an acrylic aldehyde having a formula

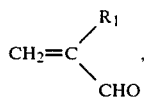

in which $R_1$ is an alkyl radical having from 1 to 4 carbon atoms, (b) from 40 to 70% by weight to total monomers of an acrylic acid derivative having a formula

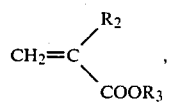

in which $R_2$ is hydrogen or an alkyl group having from 1 to 4 carbon atoms and $R_3$ is a lower hydroxyalkyl radical, (c) and less than 15% by weight of total monomers of at least one acrylic acid derivative having a formula:

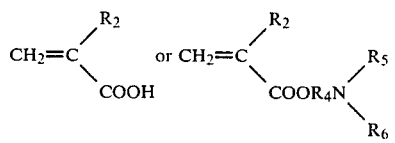

wherein $R_2$ is hydrogen or lower alkyl and $R_4$, $R_5$ and $R_6$, which may be the same or different, represent a $C_{1-4}$ alkyl group; and from 0.1 to 10% by weight of total monomers of an unconjugated diene crosslinking agent; said microparticles having coupled thereto an antibody or a fragment of an antibody having the ability to recognize the specific antigen and selected from the group consisting of polyclonal antibodies isolated from specific immune sera obtained from animals after immunization with purified $HB_s$ antigen and monoclonal antibodies produced from hybrid cells resulting from the fusion of plasmocytes of animals immunized against $HB_s$ antigen, and from myeloma cells.

10. A regent kit as claimed in claim 9, wherein the antigen is $HB_s$ antigen.

11. A reagent kit as claimed in claim 9, which has a sensitivity of the order of 0.1 ng of antigen per ml.

12. A reagent kit as claimed in claim 11, wherein the antigen is $HB_s$ antigen.

13. A method for making antibody containing polyfunctional hydrophilic spherical microparticles of uniform size having an average diameter of between about 10 nanometers and about 10 micrometers, which comprises copolymerizing:

(a) from 5 to 95% by weight of the total monomers of an acrylic aldehyde having a formula

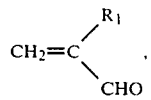

in which $R_1$ is an alkyl radical having from 1 to 4 carbon atoms, (b) from 5 to 90% by weight of total monomers of an acrylic acid derivative having a formula

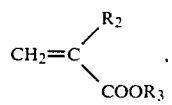

in which $R_2$ is hydrogen or an alkyl group having from 1 to 4 carbon atoms and $R_3$ is a lower hydroxyalkyl radical, (c) and less than 15% by weight of total monomers of at least one acrylic acid derivative having a formula:

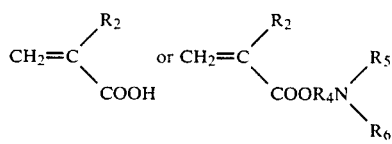

wherein $R_2$ is hydrogen or lower alkyl and $R_4$, $R_5$ and $R_6$, which may be the same or different, represent a $C_{1-4}$ alkyl group; and from 0.1 to 10% by weight of total monomers of an unconjugated diene crosslinking agent to form said microparticles and then coupling thereto an antibody selected from the group consisting of polyclonal antibodies isolated from specific immune sera obtained from animals after immunization with purified antigen and monoclonal antibodies produced from hybrid cells resulting from the fusion of plasmocytes of animals immunized against antigen, and from myeloma cells to obtain said antibody containing microparticles.

* * * * *